US008445266B2

(12) United States Patent
Kiyota et al.

(10) Patent No.: US 8,445,266 B2
(45) Date of Patent: May 21, 2013

(54) APPARATUS FOR JUDGING CELL DETACHMENT, METHOD OF JUDGING CELL DETACHMENT, AND CELL CULTURE APPARATUS

(75) Inventors: Yasujiro Kiyota, Tokyo (JP); Hiroaki Kii, Kawasaki (JP)

(73) Assignee: Nikon Corporation, Tokyo (JP)

( * ) Notice: Subject to any disclaimer, the term of this patent is extended or adjusted under 35 U.S.C. 154(b) by 196 days.

(21) Appl. No.: 12/289,595

(22) Filed: Oct. 30, 2008

(65) Prior Publication Data

US 2009/0081769 A1   Mar. 26, 2009

Related U.S. Application Data

(63) Continuation of application No. PCT/JP2007/060464, filed on May 22, 2007.

(30) Foreign Application Priority Data

May 22, 2006   (JP) .................................. 2006-141725

(51) Int. Cl.
*C12Q 1/70* (2006.01)
*C12Q 1/06* (2006.01)
*C12C 1/02* (2006.01)
*C12M 1/34* (2006.01)
*C12M 3/00* (2006.01)

(52) U.S. Cl.
USPC ................ 435/288.7; 435/6; 435/29; 435/39; 435/287.1; 435/287.2

(58) Field of Classification Search
USPC .................................. 435/288.7, 283.1–309.4
See application file for complete search history.

(56) References Cited

U.S. PATENT DOCUMENTS

| | | | |
|---|---|---|---|
| 6,631,331 B1 * | 10/2003 | Sabry et al. ..................... | 702/19 |
| 2006/0115889 A1 | 6/2006 | Nakashima et al. | |
| 2008/0176276 A1 | 7/2008 | Arai | |

FOREIGN PATENT DOCUMENTS

| | | |
|---|---|---|
| JP | A 6-508021 | 9/1994 |
| JP | A 2003-235540 | 8/2003 |
| JP | A 2003-235541 | 8/2003 |
| JP | A 2004-344049 | 12/2004 |
| JP | A 2006-149268 | 6/2006 |
| JP | A 2006-271210 | 10/2006 |
| JP | A 2006-314214 | 11/2006 |
| WO | WO 92/16614 A1 | 10/1992 |

OTHER PUBLICATIONS

Sep. 4, 2012 Office Action issued in Japanese Patent Application No. 2008-516709 w/translation.

* cited by examiner

*Primary Examiner* — Nathan Bowers
*Assistant Examiner* — Lydia Edwards
(74) *Attorney, Agent, or Firm* — Oliff & Berridge, PLC

(57) ABSTRACT

An apparatus for judging cell detachment that judges a state of detachment of cells that have been cultured within a cell culture container (cultured cells), includes: an image-capturing unit that captures an image of the cultured cells; and a detachment state judging unit that determines luminance information within the cell culture container based upon image capture data from the image-capturing unit, and judges that the culture cells are detached when the luminance information exceeds a predetermined luminance level.

22 Claims, 7 Drawing Sheets

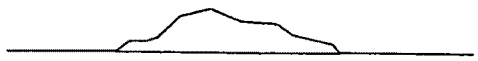
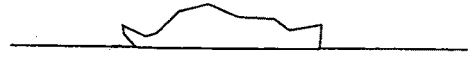
FIG.2A  FIG.2B
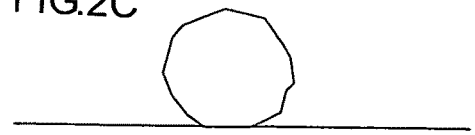
FIG.2C

CHANGE OF AREA RATIO OF REGIONS EXCEEDING THRESHOLD VALUE, AFTER ADDITION OF TRYPSIN

TIME SERIES IMAGES

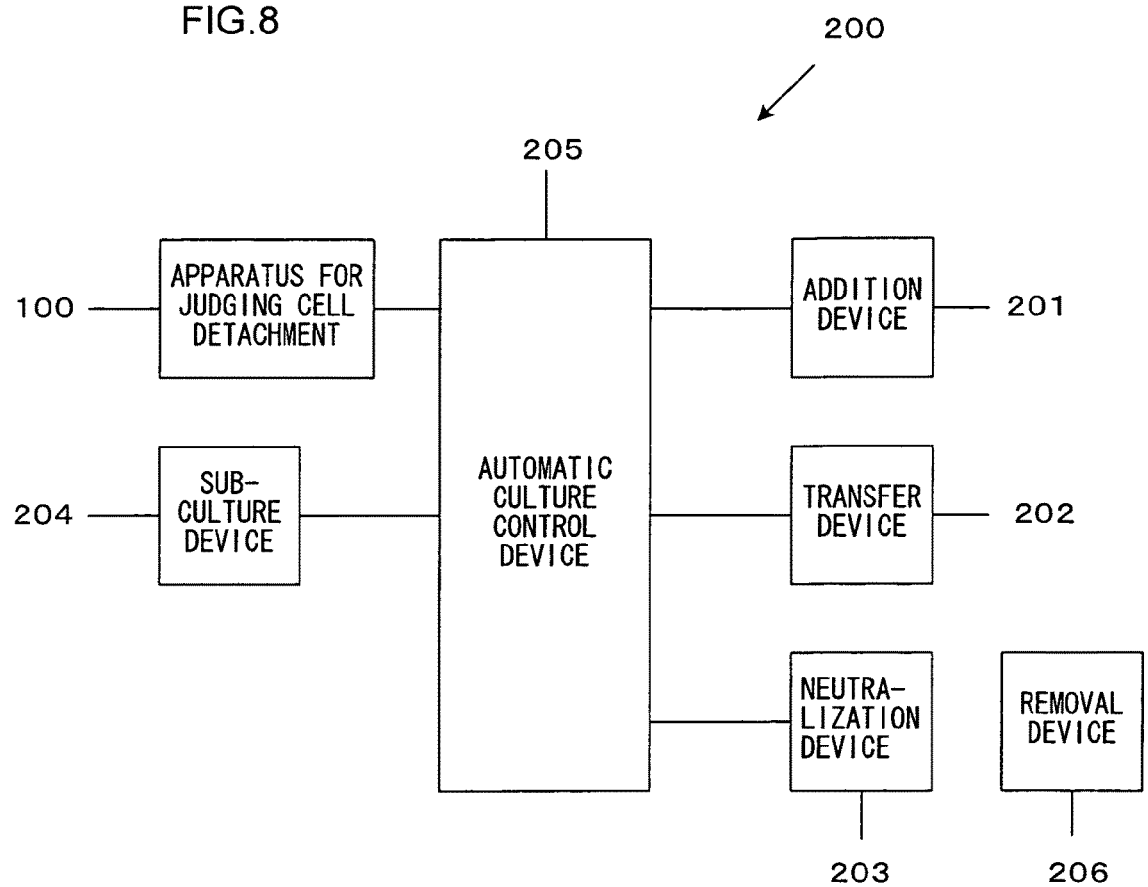

APPARATUS FOR JUDGING CELL DETACHMENT, METHOD OF JUDGING CELL DETACHMENT, AND CELL CULTURE APPARATUS

This application is a continuation of International Application No. PCT/JP2007/060464 filed May 22, 2007.

INCORPORATION BY REFERENCE

The disclosures of the following priority application and International application are herein incorporated by reference: Japanese Patent Application 2006-141725 filed May 22, 2006; and International Application No. PCT/JP2007/060464 filed May 22, 2007.

TECHNICAL FIELD

The present invention relates to an apparatus for judging cell detachment for making a judgment as to the detachment of cell adhesion, to a method of judging cell detachment, and to a cell culture apparatus that is equipped with an apparatus for judging cell detachment.

BACKGROUND ART

The following type of detached cell retrieval apparatus is known from Patent Reference #1. With this detached cell retrieval apparatus, after having added trypsin solution into a culture container, the detached cells are retrieved at the time point that a time period has elapsed that has been determined in advance as being the time period for trypsin processing.
Patent Reference #1: Japanese Laid-Open Patent Publication 2003-235541.

DISCLOSURE OF THE INVENTION

Problems to be Solved by the Invention

However, according to such a prior art device, since the time period from addition of the trypsin until detachment of the cells depends upon the type of the cells and the ambient temperature and humidity and so on, it is difficult to set it without any variation, and moreover, if the timing of retrieval of the trypsin is delayed after the cells have become sufficiently detached, there is a possibility that damage may be caused to the cells.

Means for Solving the Problems

According to the 1st aspect of the present invention, an apparatus for judging cell detachment that judges a state of detachment of cells that have been cultured within a cell culture container (cultured cells), comprises: an image-capturing unit that captures an image of the cultured cells; and a detachment state judging unit that determines luminance information within the cell culture container based upon image capture data from the image-capturing unit, and judges that the culture cells are detached when the luminance information exceeds a predetermined luminance level.
According to the 2nd aspect of the present invention, in the apparatus for judging cell detachment according to the 1st aspect, it is preferred that the luminance information is average luminance information for an entirety of the cell culture container, or a sum of luminance information for the cell culture container.

According to the 3rd aspect of the present invention, an apparatus for judging cell detachment that judges a state of detachment of cells that have been cultured within a cell culture container (cultured cells), comprises: an image-capturing unit that repeats image capture at a predetermined interval, and captures images of the cultured cells; and a detachment state judging unit that determines change of image information of the cultured cells based upon image capture data repeatedly obtained by the image-capturing unit, and judges the state of detachment of the culture cells.

According to the 4th aspect of the present invention, in the apparatus for judging cell detachment according to the 3rd aspect, it is preferred that: the apparatus further comprises a release agent addition unit that adds release agent to within the cell culture container; and the detachment state judging unit judges that the cultured cells are detached when the change of the image information of the cultured cells drops below a predetermined level.

According to the 5th aspect of the present invention, an apparatus for judging cell detachment that judges a state of detachment of cells within a cell culture container, comprises: an image-capturing unit that captures an image of the cells within the cell culture container; an area calculation unit that extracts, from image capture data of the cells captured by the image-capturing unit, regions whose luminance values are greater than or equal to a predetermined value, and calculates a total area of the regions; and a detachment state judging unit that judges the state of detachment of the cells based upon the area that has been calculated by the area calculation unit.

According to the 6th aspect of the present invention, in the apparatus for judging cell detachment according to the 5th aspect, it is preferred that the apparatus further comprises: an addition unit that adds a breakdown enzyme into the cell culture container; an information acquisition unit that acquires information specifying a state of culture of the cells within the cell culture container; and a threshold value calculation unit that calculates a threshold value for judging the state of detachment of the cells, based upon the information specifying the state of culture of the cells acquired by the information acquisition unit, and the detachment state judging unit judges the state of detachment of the cells based upon the area calculated by the area calculation unit, and upon the threshold value that has been calculated by the threshold value calculation unit.

According to the 7th aspect of the present invention, in the apparatus for judging cell detachment according to the 5th or the 6th aspect, it is preferred that the image capture data for the cells is a phase contrast image obtained by a method of phase contrast observation.

According to the 8th aspect of the present invention, in the apparatus for judging cell detachment according to any one of the 5th through 7th aspects, it is preferred that the apparatus further comprises a demand unit that, if it has been judged by the detachment state judging unit that the cells have been sufficiently detached from the cell culture container, invites neutralization of the breakdown enzyme in the cell culture container, or the elimination of the breakdown enzyme from within the cell culture container.

According to the 9th aspect of the present invention, a method of judging cell detachment for judging a state of detachment of cells that have been cultured within a cell culture container (cultured cells), comprises: capturing an image of the cultured cells; and obtaining luminance information within the cell culture container based upon image captured at a to judge that the cultured cells have been detached when the luminance information exceeds a predetermined luminance level.

According to the 10th aspect of the present invention, in the method of judging cell detachment according to the 9th aspect, it is preferred that the luminance information is average luminance information for an entirety of the cell culture container, or a sum of luminance information for the cell culture container.

According to the 11th aspect of the present invention, a method of judging cell detachment for judging a state of detachment of cells that have been cultured within a cell culture container (cultured cells), comprises: repeating image capture to capture images of the cultured cells at a predetermined interval; and obtaining a change of image information of the cultured cells based upon image data that has been repeatedly captured to judge the state of detachment of the cultured cells.

According to the 12th aspect of the present invention, in the method of judging cell detachment according to the 11th aspect, it is preferred that: the method further comprises adding a release agent into the cell culture container; and it is judged that the detachment of the cultured cells has been completed, when the change of the image information of the cultured cells drops below a predetermined level.

According to the 13th aspect of the present invention, a method of judging cell detachment for judging a state of detachment of cells within a cell culture container, comprises: capturing an image of the cells within the cell culture container; extracting regions whose luminance values are greater than or equal to a predetermined value from image capture data of the cells that have been captured, to calculate a total area of the regions; and judging the state of detachment of the cells based upon the calculated area.

According to the 14th aspect of the present invention, in the method of judging cell detachment according to the 13th aspect, it is preferred that: information is acquired specifying a state of culture of the cells within the cell culture container; a threshold value for judging the state of detachment of the cells is calculated based upon the information specifying the state of culture of the cells that has been acquired; and the state of detachment of the cells is judged based upon the area and the threshold value that have been calculated.

According to the 15th aspect of the present invention, in the method of judging cell detachment according to the 13th or the 14th aspect, it is preferred that the image capture data of the cells is a phase contrast image obtained by a method of phase contrast observation.

According to the 16th aspect of the present invention, in the method of judging cell detachment according to any one of the 13th through 15th aspects, it is preferred that: the method further comprises adding a breakdown enzyme into the cell culture container; and if it has been judged that the cells have been sufficiently detached from the cell culture container, neutralization of the breakdown enzyme in the cell culture container, or elimination of the breakdown enzyme from within the cell culture container, is invited.

According to the 17th aspect of the present invention, a cell culture apparatus comprises: an addition unit that adds a breakdown enzyme for detaching cells into a cell culture container; an apparatus for judging cell detachment according to the 8th aspect; and at least one of a neutralization unit that neutralizes the breakdown enzyme by adding the culture medium within the cell culture container when the neutralization of the breakdown enzyme has been invited from the apparatus for judging cell detachment, and an elimination unit that eliminates the breakdown enzyme from within the cell culture container when the elimination of the breakdown enzyme has been invited from the apparatus for judging cell detachment.

According to the 18th aspect of the present invention, in the cell culture apparatus according to the 17th aspect, it is preferred that the apparatus further comprises a sub-culture unit that performs sub-culture of the cells, after the neutralization of the breakdown enzyme has been performed by the neutralization unit, or the elimination of the breakdown enzyme has been performed by the elimination unit.

According to the 19th aspect of the present invention, an apparatus for judging cell detachment that judges a state of detachment of cells that have been cultured within a cell culture container (cultured cells), comprises: an image-capturing unit that repeatedly captures images of the cultured cells within the cell culture container; and a detachment state judging unit that judges that the cultured cells are detached, based upon the image information captured by the image-capturing unit.

According to the 20th aspect of the present invention, a method of judging cell detachment for judging a state of detachment of cells that have been cultured within a cell culture container (cultured cells), comprises: capturing images of the cultured cells within the cell culture container repeatedly; and judging that the cultured cells have become detached based upon information in the images that have been captured.

Advantageous Effect of the Invention

Accordingly to the present invention, since the state of detachment of the cells is judged based upon an image of the cells within the cell culture container, it is possible to judge the state of detachment of the cells with high accuracy, irrespective of the various conditions such as the type of the cells and so on.

BRIEF DESCRIPTION OF THE DRAWINGS

FIGS. 2A-2C are figures schematically showing change of cell state of detachment as seen from the side surface of a cell culture container A;

FIG. 8 is a figure showing the structure of an automatic culture device 200.

BEST METHOD FOR CARRYING OUT THE INVENTION

Figure 1:
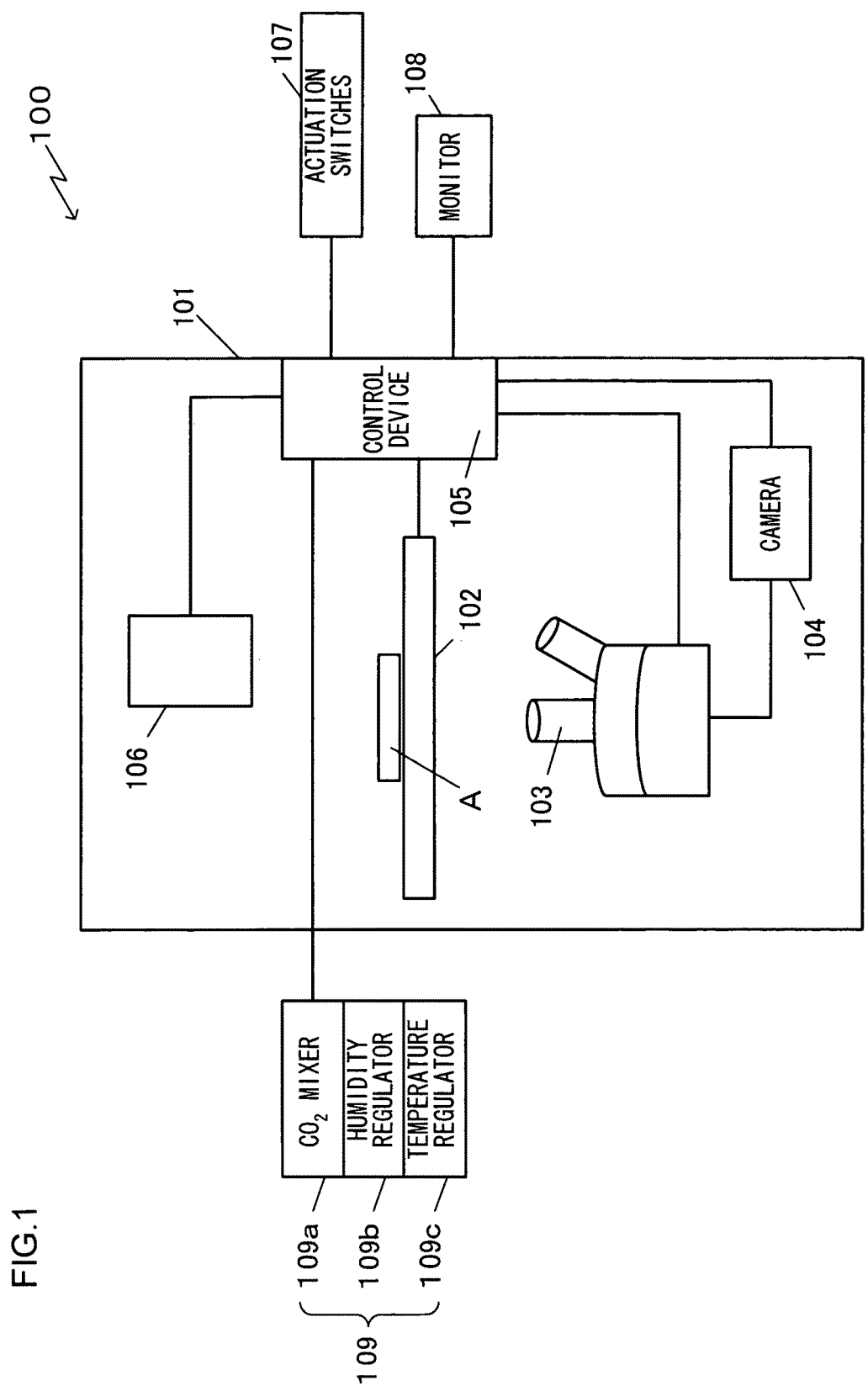
FIG. 1 is a block diagram showing the structure of an embodiment of an apparatus for judging cell detachment.

FIG. 1 is a block diagram showing the structure of an apparatus for judging cell detachment according to this embodiment. This apparatus for judging cell detachment 100 includes an incubator 101, a stage 102, an objective lens 103, a camera 104, a control device 105, an illumination device 106, actuation switches 107, a monitor 108, and an environment control device 109. It should be understood that the stage 102, the objective lens 103, the camera 104, the control device 105, and the illumination device 106 constitute a microscope.

The interior of the incubator is sealed, and its internal environment is maintained by the environment control device 109 at an environment suitable for the culture of cells. For example, the $CO_2$ density within the incubator 101 may be maintained at 5% by a $CO_2$ mixer 109a, the humidity may be maintained at 95% or greater by a humidity regulator 109b, and the temperature may be maintained at 37° C. by a temperature regulator 109c. Moreover, the stage 102, the objective lens 103, the camera 104, and the illumination device 106 are installed within the incubator 101.

A cell culture container A is mounted upon the stage 101, and constitutes the subject for judgment of the state of detachment (release) of cells, as will be described herein after. Here, for example, a 35 mm dish may be used for the cell culture container A. The illumination device 106 may include, for example, a LED as a light source, and illumination light (transmitted light) emitted by this LED is irradiated from above upon the cell culture container A.

Via the objective lens 103, and employing a phase contrast observational method, the microscope is able to observe the cells within the culture container A that has been set upon the stage 101 with light illuminated from the illumination device 106 and transmitted through the cell culture container A. The camera 104 includes an image sensor such as a CCD or the like, and captures an image of this light that is inputted via the objective lens 103, in other words an image of the light that has passed through the cell culture container A, and thereby the microscope image is captured (i.e. is photographed). By doing this, it is possible to acquire a phase contrast image.

The control device 105 includes a CPU, memory, and other peripheral circuitry, and controls the entire apparatus for judging cell detachment 100. With this apparatus for judging cell detachment 100, the user can issue various commands for the control device 105 by actuating the actuation switches 107, and the control device 105 executes various types of processing according to these commands from the user.

In the process of culturing cells within the cell culture container A, when a requirement arises for sub-culturing, or when a requirement arises for freezing for storage, it becomes necessary to detach the cells from the cell culture container A. In order to detach the cells from the cell culture container A in this manner, it is necessary to add (inject) into the cell culture container A a solution consisting of a protein breakdown enzyme, for example trypsin, mixed into PBS.

When trypsin solution is added into the cell culture container A, the cells gradually proceed to detach from the bottom surface of the cell culture container A (the container bottom surface), and, when the cells are sufficiently detached, the user retrieves the cells and performs sub-culture or freezing thereof. It is known that, if at this time the cell detachment time becomes long, then the protein breakdown enzyme not only detaches the adhesion surfaces of the cells, but also exerts a negative influence upon the cell membranes, so that the state of cellular activity becomes poor. Due to this, when retrieving the cells, it is necessary to neutralize the trypsin solution by injecting the culture medium within the cell culture container A at the optimum timing at which the cells are sufficiently detached from the bottom surface of the container. It should be understood that although, instead of neutralizing the trypsin solution, it would also be acceptable to absorb the culture solution in order to get rid of the added trypsin solution, nevertheless, in the following explanation, the case of neutralizing the trypsin solution will be explained.

Here, the time period from when the trypsin solution is added until the cells are sufficiently detached varies according to the circumstances at that time, such as the type of cells within the cell culture container A, the density of the cells, the type of the culture medium, the amount of trypsin that was added, the temperature and the humidity within the incubator 101, and the like. Due to this, in the prior art, it was necessary for the user to decide upon the retrieval timing while checking the state of detachment of the cells by using a microscope, so that substantial labor was required. Moreover, while a device is also known that retrieves the cells automatically at the time point that a predetermined time period set in advance has elapsed from when the trypsin solution was added, it is difficult to determine the time period until retrieval unconditionally, since, as described above, the time period until the cells are sufficiently detached changes according to the circumstances.

Due to this, when using a prior art device, there is the problem that sometimes, if the time period until retrieval of the cells is set to be too short, it may happen that cell retrieval is performed in the state when the cells are not sufficiently detached; and conversely that sometimes, if the time period until retrieval of the cells is set to be too long, it may happen that the timing of neutralization of the trypsin solution is delayed, so that a negative influence is exerted upon the cells as a result.

In order to eliminate this type of problem, with the apparatus for judging cell detachment 100 of this embodiment, after the trypsin solution is added to the cell culture container A, the control device 105 controls the camera 104 and the illumination device 106, and photographs phase contrast images of the cell culture container A after addition of the trypsin solution repeatedly at a predetermined time interval, for example 10 seconds. And, as will be described herein after, these phase contrast images that have been photographed are image processed, and the state of detachment of the cells is judged by detecting changes of the image along with the lapse of time. It should be understood that it will be supposed that the addition of the trypsin solution into the cell culture container A is performed in advance by the user.

First, the control device 105 controls the camera 104 and the illumination device 106 in the following manner, in order to photograph the phase contrast images of the cells repeatedly as described above. That is, it controls the illumination device 106 to make the LED emit light, so as thereby to irradiate illumination light upon the cell culture container A from above. And it controls the camera 104 so as to photograph the image that is inputted through the objective lens 103 repeatedly at intervals of the predetermined time period, for example 10 seconds.

When the input of the phase contrast images starts, the control device 105 analyzes these phase contrast images, and makes judgments as to the state of detachment of the cells based upon the change over time of the phase contrast images. In concrete terms, as explained below, the control device 105 judges the state of detachment of the cells by paying attention to the fact that a correlation relationship exists between the state of detachment of the cells and the areas of the regions within the phase contrast image in which the luminance values are high. And it can judge the optimum timing at which the cells are sufficiently detached from the bottom surface of the container and moreover the trypsin solution does not exert any negative influence upon the cells, and thereby can exhibit the optimum neutralization timing for the trypsin solution.

FIGS. 2A-2C are figures schematically showing the change of the cell state of detachment as seen from the side surface of the cell culture container A. FIG. 2A shows the situation before the trypsin solution is added into the cell culture container A, in other words the normal state in which the cells are adhering to the bottom surface of the container, while FIG. 2B shows the state of detachment of the cells after a predetermined time period has elapsed from when the trypsin solution was added to the cell culture container A, for example after 30 seconds has elapsed from when the trypsin solution was added to the cell culture container A. Moreover, FIG. 2C shows the situation when a further time period has elapsed from the state shown in FIG. 2B, and the cells are in the state of being sufficiently detached from the bottom surface of the container.

When the state of detachment of the cells is as shown in FIG. 2A, overall, only regions of small phase contrast are detected in the phase contrast image that is photographed at this time, and only comparatively small changes of phase contrast are detected between successive ones of the phase contrast image that are photographed. By contrast, when the trypsin solution is added into the cell culture container A, and the state of detachment of the cells has changed to that shown in FIG. 2B, the phase contrast becomes large in the range where the cells have been detached from (and have floated upwards from) the container bottom surface 2a, so that regions come to appear in the phase contrast images in which this type of range where the phase contrast is large has been photographed. These regions upon the phase contrast images where the phase contrast is large are termed halos, and it is known that the luminance values of the image become extremely large in these halo regions, as compared to the other regions. By "halo" is meant a phenomenon in which a fringe of light is seen around an image.

Thereafter, when the detachment of the cells proceeds further, and as the state of detachment of the cells changes to the state shown in FIG. 2C, the area of the halo regions within the phase contrast images gradually gets larger. At, at the time point that the cells are sufficiently detached from the bottom surface of the container, the area of the halo regions reaches a maximum, and thereafter the area of the halo regions remains almost constant.

Figure 4A:
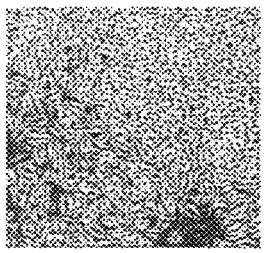
FIGS. 4A-4C are figures showing concrete examples of phase contrast images.
Figure 4B:
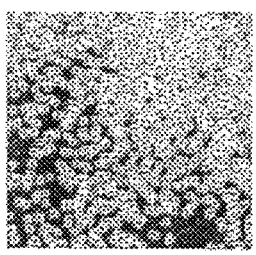
Figure 4C:
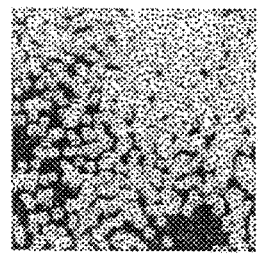

FIG. 4A is a figure showing a concrete example of a phase contrast image that has been photographed when the state of detachment of the cells is in the state shown in FIG. 2B. In this phase contrast image, the regions whose luminance is high, in other words the white regions, correspond to the halo regions. When thereafter the detachment of the cells has progressed along with the passage of time, as shown in FIG. 4B, a phase contrast image is photographed in which the area of the halo regions, in other words the area of the white regions, has become larger. And, when finally the cells are sufficiently detached and their state has changed to that shown in FIG. 2C, a phase contrast image as shown in FIG. 4C is photographed, in which the area of the halo regions is yet further enlarged.

Figure 3:
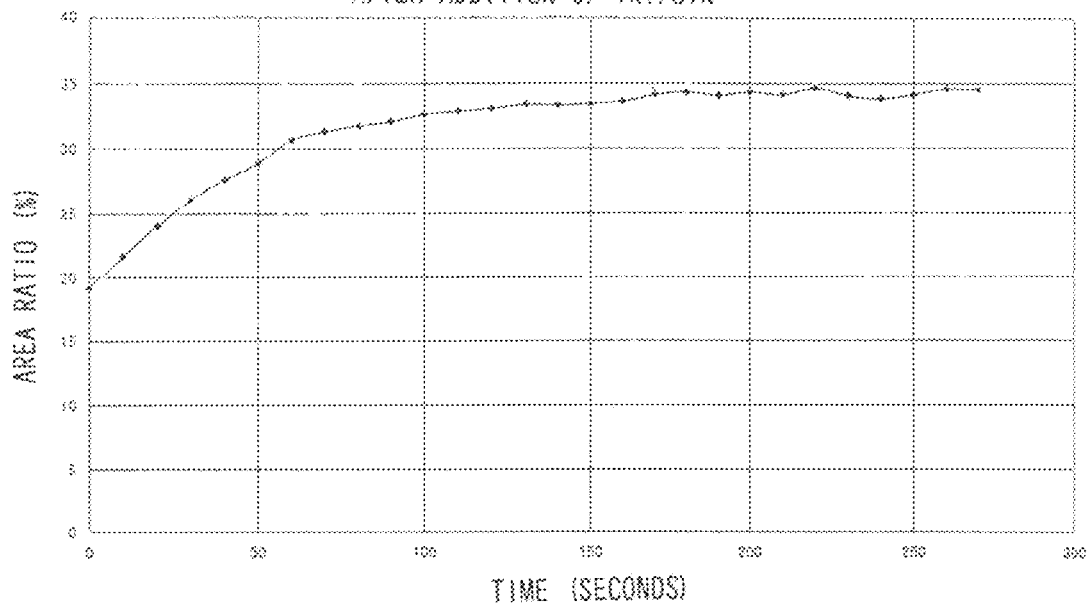
FIG. 3 is a figure showing a relationship between elapsed time from when trypsin is added to the cell culture container A, and the area ratio of a halo region.

FIG. 3 is a graph showing the relationship between the elapsed time (in seconds) from when trypsin is added to the cell culture container A, and the proportion (the area ratio in %) of the area within the base area of the cell culture container A that is occupied by the above described halo regions. It should be understood that, in this embodiment, it will be supposed that the regions for that the luminance values within the phase contrast image are greater than or equal to a predetermined value are extracted as these halo regions, and the proportion of the total of the areas of these extracted halo regions occupied within the base area of the cell culture container A is calculated as being the area ratio of the halo regions.

It will be understood that, as shown in this FIG. 3, the area ratio continues to increase during the interval until 170 seconds elapses from when the trypsin solution was added to the cell culture container A, and that accordingly the detachment of the cells is progressing. And, since the area ratio of the halo regions becomes about 34% at the time point when 170 seconds has elapsed and thereafter this ratio becomes almost constant, accordingly it may be considered that after 170 seconds the detachment of the cells progresses no further, and that, if the trypsin solution is left alone during this period and is not neutralized, then a negative influence will come to be exerted upon the cells, as described above.

Accordingly, in the example shown in this FIG. 3, it is possible to judge that, at this time point that the area ratio of the halo regions initially attains the saturation state, in other words at the time point that it reaches 34%, the cells are sufficiently detached from the bottom surface of the container, and it is possible to judge that it would be proper, at this time point, to neutralize the trypsin solution by injecting the culture medium. To put this in another manner, it is possible to judge that the time at which the area ratio of the halo regions initially reaches 34% is the above described optimum timing for neutralization of the trypsin solution.

It should be understood that the threshold value that is used for judging that the cells have been sufficiently detached (in the example of FIG. 3, 34%) changes according to the type of cells within the cell culture container A, the density of the cells, the type of the culture medium, the amount of trypsin that is added, the temperature and the humidity within the incubator 101, and so on. Accordingly, it is necessary for the control device 105, while judging the state of detachment of the cells, to acquire information that specifies the state of culture of these cells, and to calculate the threshold value according thereto. The information related to the type of cells within the cell culture container A, the density of the cells, the type of the culture medium, the amount of trypsin that is added is inputted by the user in advance for each cell culture container and is recorded, and this recorded information is read in by the control device 105. Furthermore, with regard to the temperature and the humidity within the incubator 101, this information is acquired from a thermometer and a humidity meter not shown in the figures, that are installed within the incubator 101.

And the control device calculates the threshold value based upon this information that has been acquired and that specifies the state of the cell culture. At this time, for example, it would be acceptable to perform experiments in advance under various types of environmental conditions in which the conditions described above are combined and to calculate threshold values for these various different environments, and for the control device 105 to select that one, among the threshold values that have been obtained by these experiments, that agrees with the current conditions, and to set this as the threshold value.

Based upon the correlation relationship explained above between the state of detachment of the cells and the area of the halo regions within the phase contrast image, the control device 105 performs judgment processing for the state of detachment of the cells, as will now be described. First, for each phase contrast image that is inputted in sequence, it extracts the halo regions for which the luminance value is greater than or equal to a predetermined value, and calculates the total area thereof. And, based upon this area of the halo regions that has thus been calculated, it calculates the above described area ratio of the halo regions, compares together this area ratio of the halo regions that has been calculated and the threshold value that has been calculated in advance, and decides whether or not the area ratio of the halo regions has reached the area ratio that is set as the threshold value.

And, if it has decided that the area ratio of the halo regions has reached the threshold value, then the control device 105 judges that the cells within the cell culture container A have reached a sufficiently detached state, and issues a command to the user to neutralize the trypsin solution. For example, a message may be displayed upon the monitor 108 inviting the user to neutralize the trypsin solution. By doing this, it is possible to judge the state of detachment of the cells within the cell culture container A with high accuracy, and moreover it is possible to present the optimum neutralization timing to the user.

Figure 5:
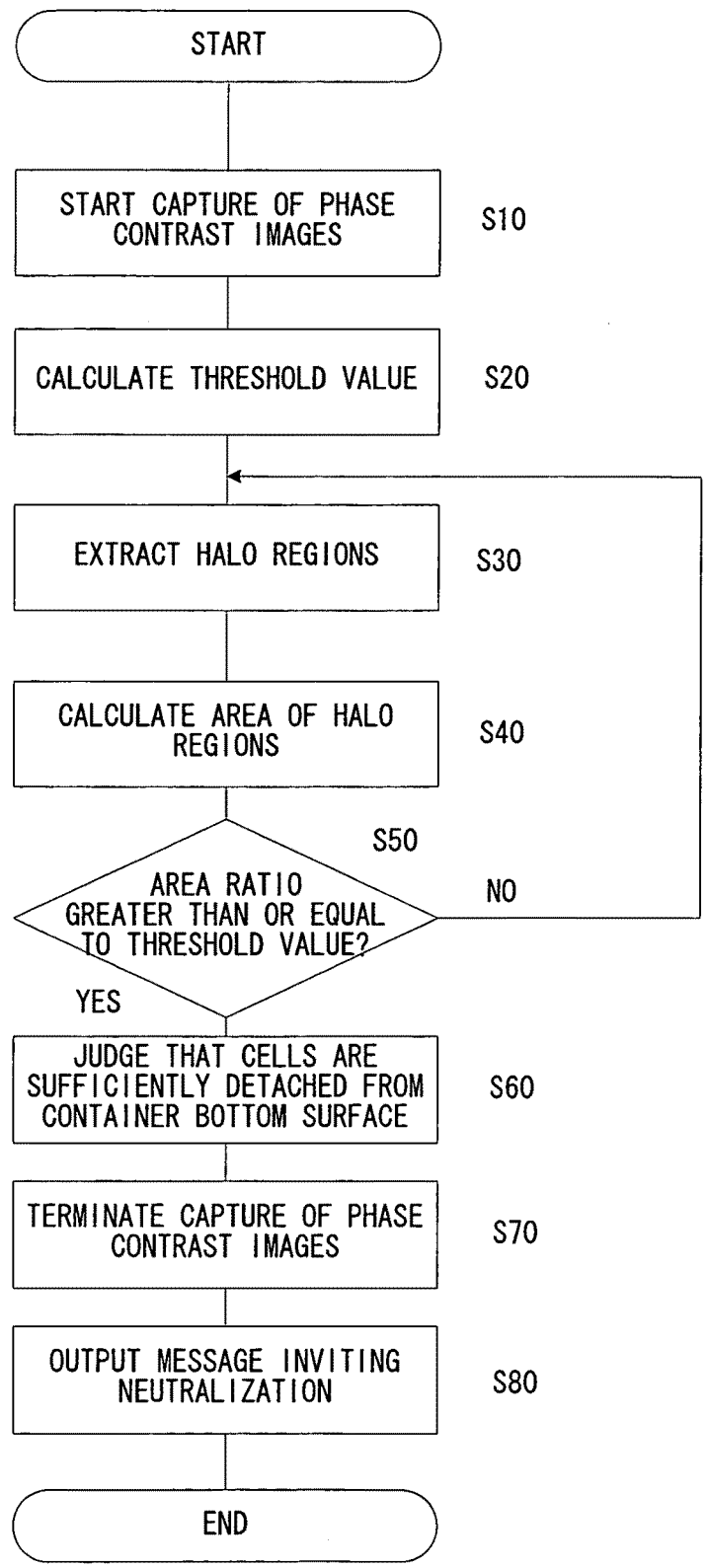
FIG. 5 is a flow chart showing the processing performed by the apparatus for judging cell detachment 100.

FIG. 5 is a flow chart showing the processing performed by the apparatus for judging cell detachment 100 of this embodiment. This processing shown in FIG. 5 is executed by the control device 105 according to a program that starts when an actuation switch 107 is actuated by the user, and a command is issued to judge the state of detachment of the cells in a cell culture container A that is set upon the stage 101. It should be understood that it will be supposed that trypsin solution is added by the user into the cell culture container A that has been set upon the stage 101 directly before, or directly after, this command is issued.

In a step S10, repeated photography of the above described phase contrast images is started. In other words, the illumination device 106 is controlled so as to make the LED emit light to irradiate illumination light upon the cell culture container A from above, and the camera 104 is controlled so as to photograph images inputted through the objective lens 103 at this time at a predetermined time interval, for example 10 seconds. Then the flow of control proceeds to a step S20, and a threshold value for judging the state of detachment of the cells is calculated based upon the above described information that specifies the state of culture of the cells. Then the flow of control proceeds to a step S30.

In the step S30, the first phase contrast image inputted from the camera 104 is read in, the halo regions within this phase contrast image in which the luminance value is greater than or equal to a predetermined value are extracted, and then the flow of control proceeds to a step S40. In this step S40, the total area of these halo regions that have been extracted from within the phase contrast image is calculated, and then the flow of control proceeds to a step S50.

In this step S50, based upon the area of the halo regions that has thus been calculated, the ratio of the area of the halo regions with respect to the base area of the cell culture container A is calculated as being the area ratio of the halo regions, and this area ratio of the halo regions and the threshold value described above that has been calculated based upon the information specifying the state of culture of the cells are compared together. As a result, it is decided whether or not the area ratio of the halo regions has reached the threshold value. If it is decided that the area ratio of the halo regions has not reached the threshold value, then the flow of control returns to the step S30 and the processing of the steps S30 through S50 is performed for the next frame of phase contrast image. By contrast, if it is decided that the area ratio of the halo regions has reached the threshold value, then the flow of control proceeds to a step S60.

In this step S60, a judgment is reached that the state of detachment of the cells in the cell culture container A has reached a sufficient state of detachment, and accordingly the flow of control proceeds to a step S70. In this step S70, the repeated photography of phase contrast images that was started in the step S10 is terminated, and then the flow of control proceeds to a step S80. In this step S80, a message is displayed upon the monitor 108 inviting the user to neutralize the trypsin solution, and then processing terminates.

According to this embodiment as explained above, the following beneficial operational effects may be obtained.

(1) It is arranged to photograph the phase contrast images of the cell culture container A after addition of the trypsin repeatedly, and to judge the state of detachment of the cells based upon changes of the phase contrast images along with the passage of time. By doing this, the labor of the user confirming the state of detachment of the cells by using a microscope, that was required in the prior art, is saved, and the convenience from the point of view of the user is enhanced.

(2) Upon each repetition of photography of a phase contrast image, the area ratio of the halo regions with respect to the entire interior of the cell culture container A is calculated, and it is arranged to make the judgment that the cells within the cell culture container A have become sufficiently detached from the bottom surface of the container, at the time point that this area ratio reaches the predetermined threshold value. Due to this, the fact is taken into account that, in the phase contrast observation, the areas where the cells in the cell culture container A are detached from the container bottom surface appear as regions in the phase contrast image where the luminance values are high, in other words the halo regions, and accordingly it is possible to judge the state of detachment of the cells with high accuracy.

(3) Each time the state of detachment of the cells is judged, it is arranged to calculate the threshold value that is used for judging that the cells are sufficiently detached based upon the information read in by the control device 105 that specifies the state of culture of the cells. Due to this, it is possible to use for this calculation a threshold value that is calculated each time and that is suitable for the cell culture container A that is the subject of judgment, so that it is possible to judge the state of detachment of the cells with high accuracy.

(4) If the result of judgment of the state of detachment of the cells is that the cells are sufficiently detached from the bottom surface of the container, then it is arranged to issue, at this time, a command to the user to neutralize the trypsin solution. By doing this, it is possible to provide this display to the user at the optimum time for neutralization, and it is possible to eliminate the bad influence upon the cells that is entailed by the elapsing of an excessive period of time after addition of the trypsin solution. Moreover, a similar advantageous effect is also obtained if a command is issued to the user to remove the trypsin solution from within the cell culture container A.

Variant Embodiments

It should be understood that the apparatus for judging cell detachment of the embodiment described above may also be varied in any of the following ways.

(1) In the embodiment described above, it is arranged for the user to perform addition of the trypsin solution to the cell culture A manually. Moreover, it is arranged for the execution command for the processing shown in FIG. 5 to be issued manually by the user. And also it is arranged to notify the user of the optimum neutralization timing, and for the user to add the culture medium into the cell culture container A manually. In other words, an example has been explained in which the user performs manual operation, apart from the processing shown in FIG. 5. However, the present invention is not limited to this feature; for example, it would be possible to mount this apparatus for judging cell detachment 100 of the embodiment described above to an automatic cell culture device, and to arrange to perform all of the processing automatically.

In concrete terms, for each cell culture A, the automatic culture device manages the timing for sub-culturing or freezing, and, after having automatically added trypsin solution to a cell culture container A for which a requirement for sub-culture or freezing has arisen, sets this cell culture container A upon the stage 102 within the incubator 101, and commands the apparatus for judging cell detachment 100 to execute the processing shown in FIG. 5. And the apparatus for judging cell detachment 100 executes the processing shown in FIG. 5 according to orders from the automatic culture device, judges the state of detachment of the cells within the cell culture container A, and judges the optimum neutralization timing for the trypsin solution according to the results of that judgment. And, at the time point that this optimum neutralization timing arrives, a signal to this effect is outputted to the automatic culture device.

The automatic culture device performs processing for sub-culturing or freezing automatically, after having taken out the cell culture container A from within the incubator 101 based upon the output signal from the apparatus for judging cell detachment 100, and after having injected culture medium into the cell culture container A to neutralize the trypsin solution. By applying this apparatus for judging cell detachment 100 to an automatic culture device in this manner, it is possible to enhance the accuracy of the processing for judging the state of detachment of cells during automatic processing.

FIG. 8 is a figure showing the structure of the automatic culture device 200 described above. This automatic culture device 200 includes the previously described apparatus for judging cell detachment 100, an addition device that adds trypsin solution to the cell culture container A, a transfer device 202 that sets the cell culture container A upon the stage 102 within the incubator 101 of the apparatus for judging cell detachment 100 and takes it out, a neutralization device 203 that adds culture medium to the cell culture container A and neutralizes the trypsin solution, a sub-culture device 204 that performs sub-culturing, and an automatic culture control device 205 that controls these units, and the like. It should be understood that, instead of the neutralization device 203, it would also be acceptable to arrange to provide a removal device 206 for removing the trypsin solution from the cell culture container A.

(2) In the embodiment described above, an example has been explained in which, when it is judged that the area ratio of the halo regions reaches a threshold value, it is judged that the cells within the cell culture container A have reached the state of being sufficiently detached, and the user is ordered to neutralize the trypsin solution. However this is not necessarily limitative of the present invention; it would also be acceptable to arrange to control the timing of ordering the user to neutralize the trypsin solution, while taking into account a preliminary time period that it takes for the user to start the task of neutralizing the trypsin solution, from when he has been commanded to neutralize the trypsin solution.

In other words, the usual preliminary time period that it takes before the user starts the task of neutralizing the trypsin solution is measured in advance and stored. And, based upon the time for change of the area ratio of the halo regions in each phase contrast image that is successively inputted, the control device 105 estimates the time instant at which the area ratio of the halo regions will arrive at the threshold value. And it will be acceptable for the control device 105 to set, as a neutralization command timing, a time instant that is obtained by subtracting the preliminary time period that has been measured in advance from this estimated time instant, and to issue to the user the command for neutralization of the trypsin solution at the time point that this neutralization command timing arrives.

By doing this, it is possible to issue to the user a neutralization command for the trypsin solution while allowing a certain clearance that takes into account the preliminary time period, so that the user can start the provision of neutralization for the trypsin solution in response to this command, and thereby it is possible to perform the task of neutralization at the optimum timing just at the moment when the state comes to pass in which the cells within the cell culture container A have become sufficiently detached. It should be understood that it would also be acceptable to apply the details of this variant embodiment to the above variant embodiment (1), so as to take into account the preliminary time period that the automatic culture device requires until starting the neutralization of the trypsin solution.

(3) While, in the embodiments described above, examples were explained in which trypsin solution is added to the cell culture container A in order to detach the cells from the bottom surface of the container, it would also be possible to apply the present invention to a case in which the cells are detached by addition of some breakdown enzyme other than trypsin.

(4) In the embodiments described above, it is arranged to judge the state of detachment of the cells by performing comparison, upon each of a sequence of phase contrast images that are photographed in succession, between the area ratio of the halo regions and a threshold value. However, it would also be acceptable to arrange to compare together a phase contrast image that has been photographed before the addition of the trypsin solution, and the phase contrast images that are successively photographed after the addition of the trypsin solution, and to judge the state of detachment of the cells based upon the area change of the halo regions before and after the addition of the trypsin solution.

(5) Although, in the embodiments described above, it was arranged to judge the state of detachment of the cells by performing image processing upon the phase contrast images that were obtained by observation of the interior of the cell culture container A by a method of phase contrast observation, it would also be possible to judge the state of detachment of the cells based upon images that are obtained by some other method of cell observation.

(6) In the embodiments described above, examples were explained in which, in order to judge the state of detachment of the cells, the area of the halo regions with respect to the base area of the cell culture container A was calculated as being the area ratio of the halo regions, and this area ratio of the halo regions and a threshold value were compared together. However, if the standard for the cell culture containers that are to be used is unified and so on, i.e. if the area within the cell culture container A is constant, it would also be acceptable to arrange to judge the state of detachment of the cells based upon the total area of the halo regions, without calculating the area ratio of the halo regions.

Furthermore, it would also be acceptable to arrange to obtain some luminance information for the interior of the cell culture container after the addition of the trypsin solution, for example the average luminance information over the entire cell culture container or the total luminance information for the cell culture container, and to judge that the detachment of the cells has been completed when this luminance information exceeds a predetermined luminance level (judgment based upon image luminance). Or, it would also be acceptable to arrange to capture images of the cells repeatedly at a predetermined time interval, and, based upon this image capture data that is obtained repeatedly, to obtain some change of the image information for the cells after addition of the trypsin solution, for example change of the shape of the cells, and to judge that the detachment of the cells has been completed when the change of this image information drops below a predetermined level (judgment based upon image shape).

Figure 6:
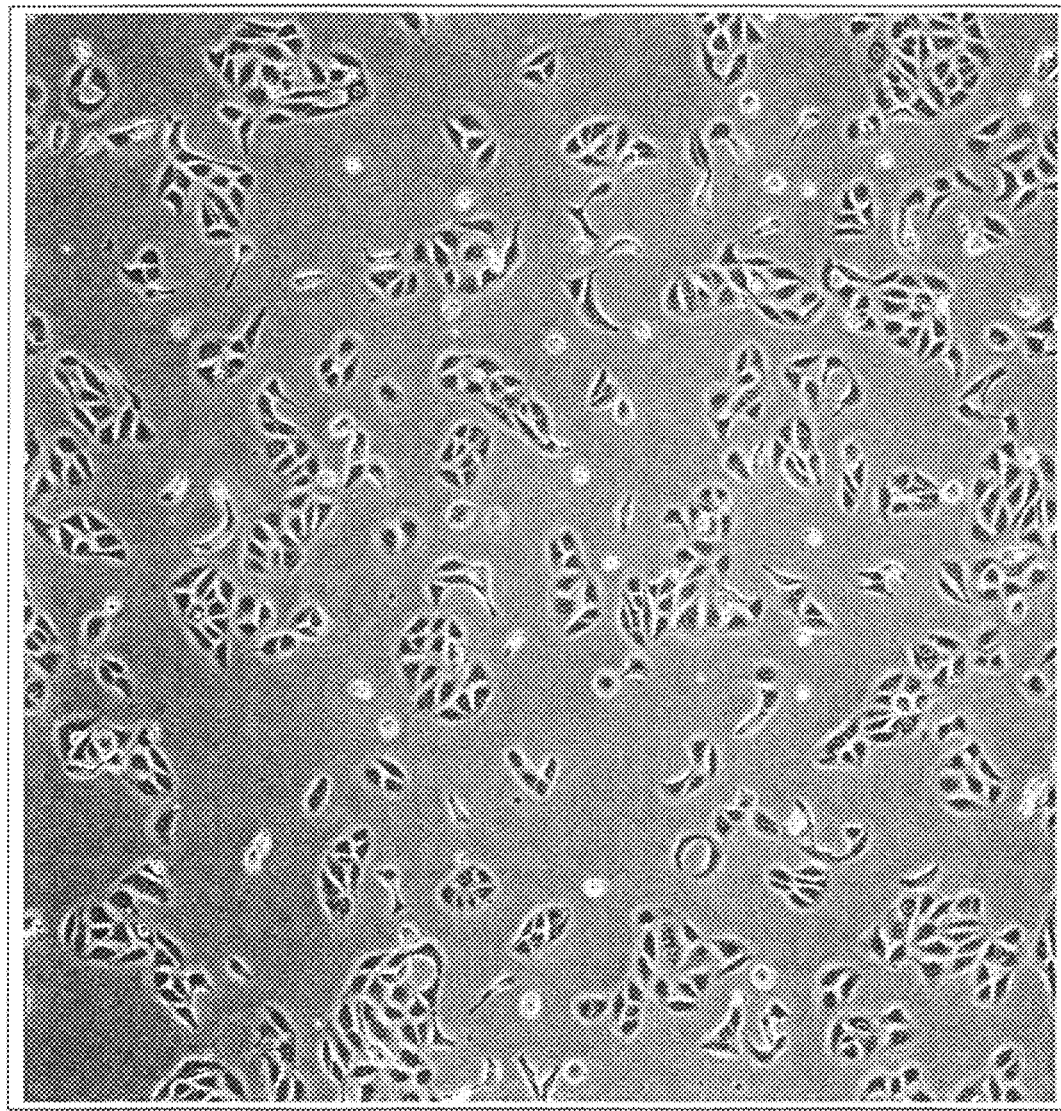
FIG. 6 is a figure illustrating a state of cell detachment.

Now, a concrete example of judgment based upon image luminance and judgment based upon image shape will be explained using FIGS. 6 and 7. FIG. 6 is a figure illustrating a state of cell detachment. The detachment of the cultured cells starts when the trypsin is added to the cell culture container A, and, for the cells that have been detached, shown by the arrows, their luminance levels are higher than those of the cells that are still adhered to the cell container A (i.e. that have not yet been detached), while their shapes are deformed into circular shapes. In this variant embodiment, the detachment of the cells is judged by taking these facts into account, and the timing for neutralizing the trypsin solution or for eliminating the culture solution (i.e. the timing for performing absorption processing) is determined accordingly.

Figure 7:
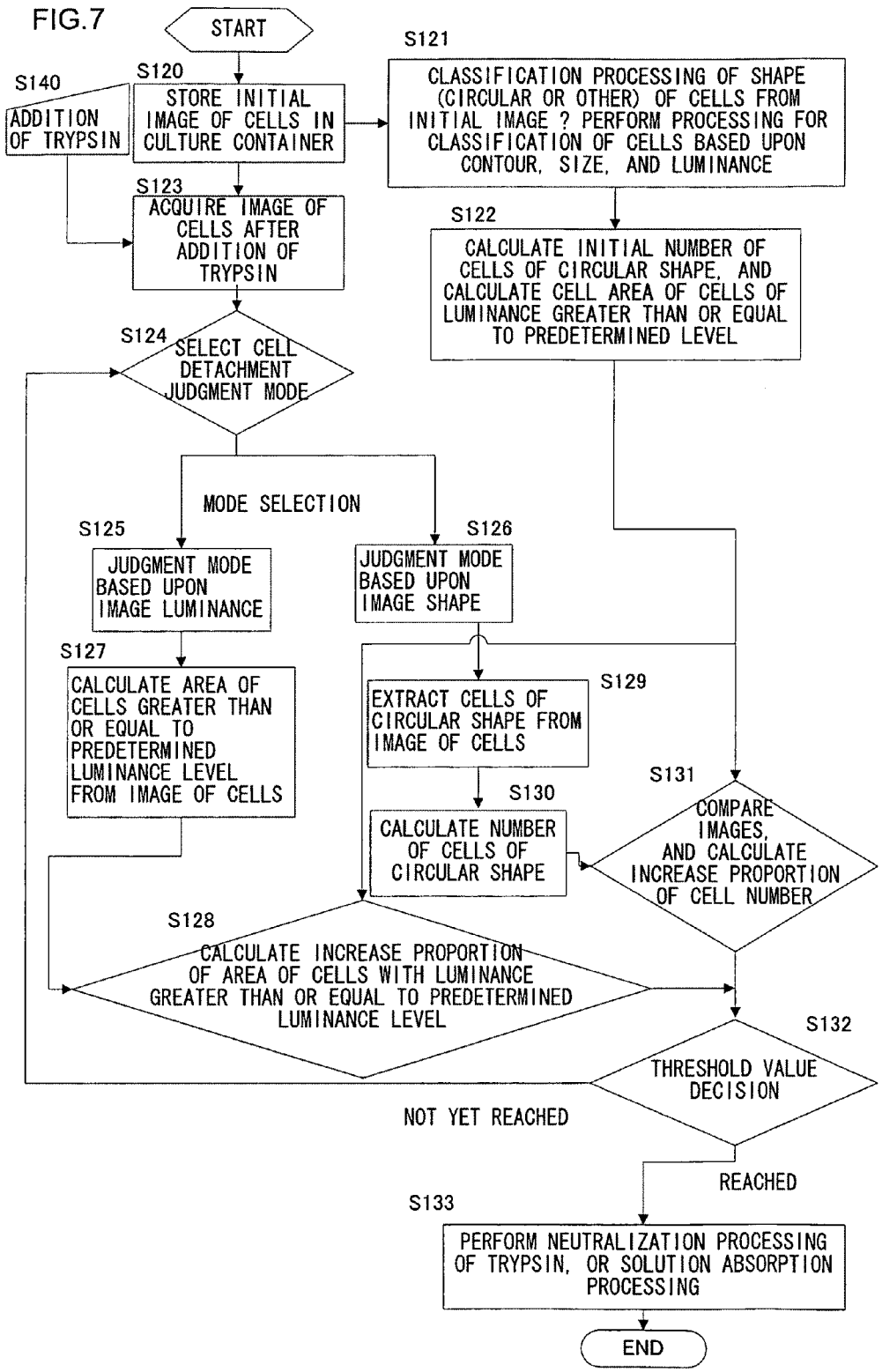
FIG. 7 is a flow chart showing the flow of processing for judgment based upon image luminance and judgment based upon image shape.

FIG. 7 is a flow chart showing the flow of processing for judgment based upon image luminance and for judgment based upon image shape. In a step S120, an image of the cells in the cell culture container A is captured, and is stored as an initial image within the memory provided to the control device 105. Then the flow of control proceeds to a step S121, in which this initial image that has been acquired is analyzed, and the cells in the cell culture container A are classified based upon their contours, shapes, luminance, and size. In concrete terms, those cells that are of circular shapes, and those cells whose luminance is greater than a predetermined level, are extracted. Then the flow of control proceeds to a step S122, in which the number of the cells of circular shape, and the area of the cells whose luminance is greater than the predetermined level, extracted in the step S121, are calculated. It should be understood that, in order to perform these measurements more accurately, the area of those cells that are of circular shape and also whose luminance is greater than the predetermined level may be calculated. Then the flow of control is transferred to a step S131 that will be described herein after.

On the other hand, when in a step S140 the trypsin solution is added into the cell culture container A, the detachment of the cells in the cell culture container A starts to proceed. Thus, in a step S123, images of the cells are sequentially acquired by intermittently photographing this state of detachment, and are stored in the memory provided to the control device 105. Then the flow of control proceeds to a step S124, in which it is decided which, of a judgment mode based upon image luminance and a judgment mode based upon image shape, is set as the cell detachment judgment mode. It should be understood that these modes are set by the user.

If it has been decided that the mode of judgment based upon image luminance has been set by the user as the cell detachment judgment mode, then the flow of control proceeds to a step S125, in which processing for the judgment mode based upon image luminance is started, and then the flow of control proceeds to a step S127. In this step S127, the area of cells whose luminance is greater than or equal to a predetermined luminance level is calculated from an image of the cells after the addition of the trypsin solution. Here as well, if a more accurate measurement is to be performed, then the area of those cells that are of circular shape and also whose luminance is greater than the predetermined level may be calculated.

Then the flow of control proceeds to a step S128, and the ratio of the area of the cells whose luminance is greater than or equal to the predetermined luminance level in the image of the cells after the addition of the trypsin solution, that was calculated in the step S127, and the area of the cells whose luminance is greater than or equal to the predetermined luminance level in the initial image, that was calculated in the step S122, in other words the area ratio, is calculated according to the following Equation (1).

Area ratio=(area of the cells whose luminance is greater than or equal to the predetermined luminance level in the image of the cells after the addition of the trypsin solution)/(area of the cells whose luminance is greater than or equal to the predetermined luminance level in the initial image)   (1)

This processing is executed upon each image that is acquired in succession after the addition of the trypsin solution, and the increase proportion of the area ratio between the images is calculated. Then the flow of control is transferred to a step S132 that will be described herein after.

On the other hand, if it has been decided that the mode of judgment based upon image shape has been set by the user as the cell detachment judgment mode, then the flow of control proceeds to a step S126, in which processing for the judgment mode based upon image shape is started, and then the flow of control proceeds to a step S129. In this step S129, the cells of circular shape are extracted from the image of the cells after the addition of the trypsin solution, based upon the contour, the shape, the size, the luminance and so on of the cells. Then the flow of control proceeds to a step S130 in which the number of the cells of circular shape that have thus been extracted is calculated, and then the flow of control proceeds to a step S131.

In this step S131, the ratio of the number of cells of circular shape in the image of the cells after the addition of the trypsin solution, that was calculated in the step S130, and the number of cells of circular shape in the initial image of the cells, that was calculated in the step S122, is calculated according to the following Equation (2) below.

Cell number ratio=(number of cells of circular shape in the image of the cells after the addition of the trypsin solution)/(number of cells of circular shape in the initial image)   (2)

This processing is executed upon each image that is acquired in succession after the addition of the trypsin solution, and the increase proportion of the ratio of the numbers of cells of circular shape between the images is calculated. Then the flow of control is transferred to the step S132.

In this step S132, the state of detachment of the cells is judged based upon either one of the increase proportion of the area ratio between the images, as calculated in the step S128, and the increase proportion of the number of cells of circular shape between the images, as calculated in the step S131. In other words it is judged that the detachment of the cells has proceeded sufficiently, at the time point that it is judged that the increase proportion of the area ratio between the images, or the increase proportion of the number of cells of circular shape between the images, has become smaller than a predetermined rate of change (i.e. a predetermined threshold value). By doing this, it is possible to judge the state of detachment of the cells at high accuracy, by paying attention to the facts that, as the detachment of the cells progresses, along with decrease of the rate of detachment of the cells, the rate of change of the luminance of the cells decreases, and also the rate of change of the shapes of the cells decreases.

When it has been judged that the detachment of the cells has proceeded sufficiently, then the flow of control proceeds to a step S133 in which the above described processing to neutralize the trypsin, or to absorb the culture solution, is executed; and then this processing terminates.

As has been explained above, with the apparatus for judging cell detachment according to the embodiment and the variant embodiments described above, it is arranged to judge the state of detachment of the cells based upon image information in the images that are captured by the camera 104. This image information may be, for example, luminance information for each pixel in the images. Based upon this luminance information, it is possible to obtain luminance values for the entire images or for predetermined regions, and it is possible to determine the state of detachment of the cells according to whether or not the luminance value is greater than a predetermined value, or according to whether or not the change of this luminance value is smaller than a predetermined value. Moreover, based upon this luminance information, it is possible to obtain the areas (the halo areas) in which the luminance values are greater than or equal to a predetermined value, and it is possible to decide upon the state of detachment of the cells according to whether or not these areas are greater than or equal to a predetermined value.

It should be understood that, the present invention is not in any way limited to the structure of the embodiment described above, provided that the characteristic function of the present invention is not lost. Other modes are also included within the range of the present invention, provided that it is considered that these modes remain within the range of the technical concept of the present invention.

The invention claimed is:

1. An apparatus for determining cell detachment that determines a state of detachment from a cell culture container of cultured cells that have been cultured within the cell culture container, comprising:
   an image-capturing unit that captures an image of the cultured cells; and
   a controller that is programmed to determine the state of detachment of the cultured cells by detecting a change of image information of the cultured cells based upon image capture data from the image-capturing unit, and to issue a command to neutralize a breakdown enzyme in the cell culture container or to eliminate the breakdown enzyme from within the cell culture container when the controller determines that the cultured cells are detached.

2. An apparatus for determining cell detachment according to claim 1, wherein
   the controller detects the change of the image information of the cultured cells based upon the image capture data repeatedly obtained by the image-capturing unit, and determines that the cultured cells are detached when the change of the image information of the cultured cells drops below a predetermined level.

3. An apparatus for determining cell detachment according to claim 1, wherein:
   the image information of the cultured cells includes luminance information within the cell culture container, and
   the controller obtains the luminance information within the cell culture container based upon the image capture data from the image-capturing unit, and determines that the culture cells are detached when the luminance information exceeds a luminance threshold value.

4. An apparatus for determining cell detachment according to claim 3, wherein
   the luminance information is an average luminance information for an entirety of the cell culture container, or a sum of the luminance information for the cell culture container.

5. An apparatus for determining cell detachment according to claim 4, wherein
   the controller calculates timing, at which the command to neutralize the breakdown enzyme in the cell culture container or to eliminate the breakdown enzyme from within the cell culture container is issued, by comparing the luminance information within the cell culture container and the luminance threshold value.

6. An apparatus for determining cell detachment according to claim 5, wherein
   the controller acquires information specifying a state of culture of the cultured cells within the cell culture container, and calculates the luminance threshold value varying according to the state of culture of the cultured cells based upon the acquired information specifying the state of culture of the cultured cells.

7. An apparatus for determining cell detachment according to claim 6, wherein
   the state of culture of the cultured cells includes at least one of a type of the cultured cells within the cell culture container, a density of the cultured cells within the cell culture container, a type of a culture medium where the cultured cells are cultured, an amount of breakdown enzyme in case of addition, a temperature while culturing and a humidity while culturing.

8. An apparatus for determining cell detachment according to claim 7, wherein
   the controller calculates a time period from issuing the command to neutralize the breakdown enzyme in the cell culture container or to eliminate the breakdown enzyme to start neutralizing the breakdown enzyme in the cell culture container or eliminating the breakdown enzyme from within the cell culture container, and issues the command to neutralize the breakdown enzyme in the cell culture container or to eliminate the breakdown enzyme from within the cell culture container from the calculated time period.

9. An apparatus for determining cell detachment according to claim 8, wherein
   the controller determines the state of detachment of the cultured cells by extracting, from the image capture data of the cultured cells captured by the image-capturing unit, regions whose luminance values are greater than or equal to a predetermined value, calculating a total area of the regions, and obtaining the luminance information within the cell culture container based upon the calculated total area.

10. An apparatus for determining cell detachment according to claim 9, wherein
    the image capture data for the cultured cells is a phase contrast image obtained by a method of phase contrast observation.

11. A cell culture apparatus, comprising:
    an addition unit that adds a breakdown enzyme for detaching cultured cells into a cell culture container;
    an apparatus for determining cell detachment according to claim 1; and
    at least one of a neutralization unit that neutralizes the breakdown enzyme in the cell culture container and an elimination unit that eliminates the breakdown enzyme from within the cell culture container, based upon the command from the controller.

12. A cell culture apparatus according to claim 11, further comprising:
    a sub-culture unit that performs sub-culture of the cultured cells, after the neutralization of the breakdown enzyme is performed by the neutralization unit, or the elimination of the breakdown enzyme is performed by the elimination unit.

13. A method for determining cell detachment that determines a state of detachment from a cell culture container of cultured cells that have been cultured within the cell culture container, comprising:
   capturing, by an image-capturing unit, an image of the cultured cells;
   determining, by a controller, the state of detachment of the cultured cells by detecting a change of image information of the cultured cells based upon image capture data from the image-capturing unit; and
   issuing, by the controller, a command to neutralize a breakdown enzyme in the cell culture container or to eliminate the breakdown enzyme from within the cell culture container when the controller determines that the cultured cells are detached.

14. A method for determining cell detachment according to claim 13, wherein
   the controller detects the change of the image information of the cultured cells based upon the image capture data repeatedly obtained by the image-capturing unit, and determines that the cultured cells are detached when the change of the image information of the cultured cells drops below a predetermined level.

15. A method for determining cell detachment according to claim 13, wherein:
   the image information of the cultured cells includes luminance information within the cell culture container, and
   the controller obtains the luminance information within the cell culture container based upon the image capture data from the image-capturing unit, and determines that the culture cells are detached when the luminance information exceeds a luminance threshold value.

16. A method for determining cell detachment according to claim 15, wherein
   the luminance information is an average luminance information for an entirety of the cell culture container, or a sum of the luminance information for the cell culture container.

17. A method for determining cell detachment according to claim 16, wherein
   the controller calculates timing, at which the command to neutralize the breakdown enzyme in the cell culture container or to eliminate the breakdown enzyme from within the cell culture container is issued, by comparing the luminance information within the cell culture container and the luminance threshold value.

18. A method for determining cell detachment according to claim 17, wherein
   the controller acquires information specifying a state of culture of the cultured cells within the cell culture container, and calculates the luminance threshold value varying according to the state of culture of the cultured cells based upon the acquired information specifying the state of culture of the cultured cells.

19. A method for determining cell detachment according to claim 18, wherein
   the state of culture of the cultured cells includes at least one of a type of the cultured cells within the cell culture container, a density of the cultured cells within the cell culture container, a type of a culture medium where the cultured cells are cultured, an amount of breakdown enzyme in case of addition, a temperature while culturing and a humidity while culturing.

20. A method for determining cell detachment according to claim 19, wherein
   the controller calculates a time period from issuing the command to neutralize the breakdown enzyme in the cell culture container or to eliminate the breakdown enzyme to start neutralizing the breakdown enzyme in the cell culture container or eliminating the breakdown enzyme from within the cell culture container, and issues the command to neutralize the breakdown enzyme in the cell culture container or to eliminate the breakdown enzyme from within the cell culture container from the calculated time period.

21. A method for determining cell detachment according to claim 20, wherein
   the controller determines the state of detachment of the cultured cells by extracting, from the image capture data of the cultured cells captured by the image-capturing unit, regions whose luminance values are greater than or equal to a predetermined value, calculating a total area of the regions, and obtaining the luminance information within the cell culture container based upon the calculated total area.

22. A method for determining cell detachment according to claim 21, wherein
   the image capture data for the cultured cells is a phase contrast image obtained by a method of phase contrast observation.

* * * * *